(12) United States Patent
Subramaniam et al.

(10) Patent No.: US 8,827,952 B2
(45) Date of Patent: Sep. 9, 2014

(54) BIASING MECHANISM FOR A BALLOON CATHETER

(75) Inventors: Raj Subramaniam, Fremont, CA (US); Zaya Tun, Livermore, CA (US); Desmond Cheung, San Jose, CA (US); Robert Quintos, Newark, CA (US)

(73) Assignee: Boston Scientific Scimed, Inc., Maple Grove, MN (US)

( * ) Notice: Subject to any disclaimer, the term of this patent is extended or adjusted under 35 U.S.C. 154(b) by 246 days.

(21) Appl. No.: 13/312,725

(22) Filed: Dec. 6, 2011

(65) Prior Publication Data
US 2012/0143130 A1 Jun. 7, 2012

Related U.S. Application Data

(60) Provisional application No. 61/420,221, filed on Dec. 6, 2010.

(51) Int. Cl.
*A61M 29/00* (2006.01)
*A61M 25/10* (2013.01)

(52) U.S. Cl.
CPC .................................. *A61M 25/10* (2013.01); *A61M 2025/1068* (2013.01)
USPC ...................................................... 604/99.01

(58) Field of Classification Search
CPC ............... A61M 2025/1013; A61M 2025/105; A61M 25/10; A61M 25/005; A61M 25/1018
USPC ............. 604/101.02, 101.01, 101.03, 99.01, 604/103.01, 103.09, 526, 97.01, 96.01, 604/103.03; 606/21
See application file for complete search history.

(56) References Cited

U.S. PATENT DOCUMENTS

| 4,838,268 | A | 6/1989 | Keith et al. |
| 4,994,032 | A * | 2/1991 | Sugiyama et al. ....... 604/103.09 |
| 5,423,755 | A | 6/1995 | Kesten et al. |
| 7,896,840 | B2 | 3/2011 | Spencer |
| 7,976,496 | B2 | 7/2011 | Kennedy |
| 8,043,313 | B2 * | 10/2011 | Krolik et al. .................. 606/159 |
| 2009/0299356 | A1 * | 12/2009 | Watson ........................... 606/21 |
| 2010/0076402 | A1 * | 3/2010 | Mazzone et al. .............. 604/509 |

* cited by examiner

*Primary Examiner* — Nicholas Lucchesi
*Assistant Examiner* — Brooke Matney
(74) *Attorney, Agent, or Firm* — Seager, Tufte & Wickhem, LLC

(57) ABSTRACT

Methods and devices for biasing a balloon catheter are disclosed. In one example, a medical device may include a catheter shaft and a balloon assembly coupled to a distal region of the catheter shaft. The balloon assembly can define a chamber configured to be inflated and deflated using a fluid supplied from the catheter shaft. A biasing member may be positioned in the chamber of the balloon assembly and may be configured to bias the balloon assembly to a longitudinally extended state without obstructing an exhaust lumen of the catheter shaft. In some cases, the biasing member may be a spring. In other cases, the biasing member may be a coiled portion of a fluid supply line.

11 Claims, 4 Drawing Sheets

BIASING MECHANISM FOR A BALLOON CATHETER

CROSS-REFERENCE TO RELATED APPLICATIONS

This application claims the benefit of U.S. Provisional Application Ser. No. 61/420,221, filed Dec. 6, 2010, the entire disclosure of which is incorporated herein by reference.

FIELD

The present disclosure relates generally to medical devices and, more particularly, to methods and devices for biasing a balloon of a balloon catheter.

BACKGROUND

A number of medical conditions may be treated in a minimally invasive manner with various kinds of catheters designed to reach treatment sites internal to a patient's body. Balloon catheters, for example, may be employed in angioplasty procedures to widen obstructed blood vessels and optionally deliver stents, or in procedures to treat atrial fibrillation, atrial flutter and ventricular tachycardia by forming therapeutic lesions in the soft tissue in the heart. In some procedures, expansion of the balloon at the treatment site may provide the desired therapy, such as expanding an obstructed blood vessel during an angioplasty procedure. In other procedures, an energy source within the balloon can deliver the desired therapy and, in these procedures, the balloon can serve to either position the energy source or communicate energy to or from the soft tissue to form the desired therapeutic lesions. For example, in procedures for treating atrial fibrillation, a balloon catheter can be used to position a radio frequency energy source in proximity to the tissue to be treated and, similarly, in cryoablation procedures for treating atrial fibrillation, a balloon catheter can be used to deliver cryotherapy or extract heat, through the surface of the balloon, from the soft tissue.

BRIEF SUMMARY

The present disclosure relates generally to medical devices and, more particularly, to methods and devices for biasing a balloon of a balloon catheter. In one illustrative embodiment, a medical device may include a catheter shaft including a first tubular member and a second tubular member. The first tubular member may include a proximal region and a distal region and the second tubular member may include a proximal region, a distal region, and a lumen extending therethrough. The catheter shaft may define an exhaust lumen between an inner surface of the outer tubular member and an outer surface of the inner tubular member. A balloon assembly may be disposed about a distal region of the elongate shaft, wherein the balloon assembly includes a proximal end coupled to a distal region of the outer tubular member and a distal end connected to a distal region of the inner tubular member. The balloon assembly may define a chamber in fluid communication with the exhaust region. A biasing member can be disposed in the chamber of the balloon assembly and may be connected to the inner tubular member and the outer tubular member. The biasing member may be configured to bias the balloon assembly to a longitudinally extended state. In some cases, the biasing member may be a spring. In other cases, the biasing member may be a coiled portion of a fluid supply tube. In some instances, the medical device may be a cryotherapy balloon catheter and the balloon assembly may include an outer balloon disposed around an inner balloon.

In another embodiment, a method of biasing a balloon catheter is disclosed. The method may include providing a catheter shaft including an outer tubular member disposed around an inner tubular member and coupling a proximal waist of a balloon assembly to the outer tubular member and a distal waist of the balloon assembly to the inner tubular member. The method may also include biasing the balloon assembly to a longitudinally extended state with a biasing member disposed in a chamber defined by the balloon assembly. The method may also include inflating the balloon assembly with a cooling fluid to overcome the bias and move the balloon assembly into a radially expanded state and exhausting the cooling fluid from the balloon assembly to move the balloon assembly to the longitudinally extended state. In some cases, the biasing member may be a spring or a coiled portion of a fluid supply tube.

The preceding summary is provided to facilitate an understanding of some of the innovative features unique to the present disclosure and is not intended to be a full description. A full appreciation of the disclosure can be gained by taking the entire specification, claims, drawings, and abstract as a whole.

BRIEF DESCRIPTION OF THE DRAWINGS

The disclosure may be more completely understood in consideration of the following detailed description of various illustrative embodiments of the disclosure in connection with the accompanying drawings, in which.

DETAILED DESCRIPTION

Figure 1:
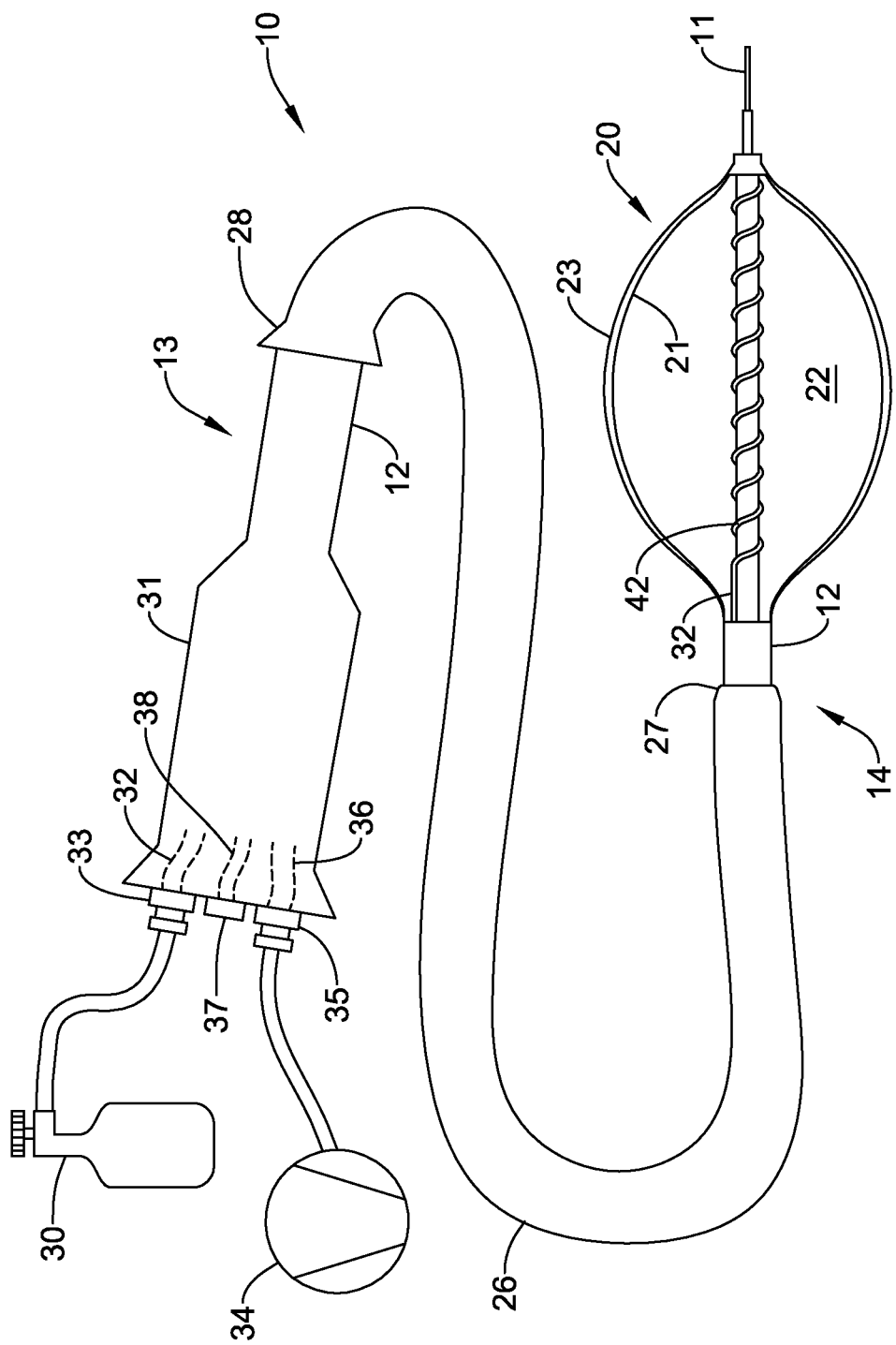
FIG. 1 is a schematic diagram of an illustrative embodiment of a balloon catheter.

The following description should be read with reference to the drawings wherein like reference numerals indicate like elements throughout the several views. The detailed description and drawings, which are not necessarily drawn to scale, show several embodiments which are meant to be illustrative and are not intended to limit the scope of the disclosure.

FIG. 1 is a schematic diagram of an illustrative embodiment of a balloon catheter 10. In the illustrative embodiment, the balloon catheter 10 may includes an elongate shaft 12 having a proximal section 13 and a distal section 14. An inflatable balloon assembly 20 may be disposed about at least a portion of the distal section 14 of the elongate shaft 12. As shown in FIG. 1, the balloon assembly 20 includes two balloons, an inner balloon 21 and an outer balloon 23. In the illustrative embodiment, the inner balloon 21 may define a chamber 22 for receiving a fluid (e.g. cryogenic fluid) and the outer balloon 23 may be disposed around the inner balloon 21. In some cases, the outer balloon 23 may function as a safety balloon to prevent the fluid from leaking out of the balloon assembly 20. That is, in the event that the inner balloon 21 ruptures or otherwise fails, the outer balloon 23 can prevent fluid (e.g., cryogenic fluid) from leaking out of the balloon assembly 20 and contacting body tissue internal to the patient.

In some embodiments, the inner balloon 21 and the outer balloon 23 may be configured to be inflated and deflated together or simultaneously, but this is not required. In other embodiments, separate inflation lumens (not shown) may be provided to independently inflate and deflate the inner balloon 21 and the outer balloon 23, as desired.

In the illustrative embodiment, inner balloon 21 and outer balloon 23 may be formed of any suitable material. For example, the inner balloon 21 and outer balloon 23 may be formed of any suitable non-compliant balloon materials. In other words, the inner balloon 21 and outer balloon 23 may be constructed to expand to a desired shape when pressurized without elastically deforming substantially beyond the desired shape. Example materials may include, for example, a polymer including but not limited to polyolefin copolymer, polyester, polyethylene teraphthalate, polyethylene, polyether-block-amide, polyamide (e.g. nylon), polyimide, latex, a urethane-family material, neoprene, etc. An example polyether-block-amide is available under the trade name PEBAX®. However, the foregoing materials are merely illustrative and it is contemplated that any suitable materials, either compliant or non-compliant, may be used. In some embodiments, inner balloon 21 and outer balloon 23 may be formed from the same or different material(s), as desired.

As illustrated in FIG. 1, the proximal section 13 of the balloon catheter 10 may include a port component 31 including a number of coupling members, such as coupling member 33 and 35, to facilitate coupling the balloon catheter 10 to external equipment. Example external equipment may include, for example, a source 30 of a cryogenic agent, a vacuum pump 34, and/or other desired external equipment. The coupling members 33 and 35 may be configured to be fluidly connected to and terminate at one or more lumens of the catheter shaft 12, such as a supply lumen 32 and an exhaust lumen 36. It is contemplated that the port component 31 may include additional coupling components fluidly connected to additional lumens, such as, for example, vacuum lumens, sensor lumens (e.g. pressure, temperature, etc.), and/or other lumens or combinations thereof. Further, the foregoing port component 31 is merely illustrative and is not meant to be limiting in any manner. It is contemplated that other suitable port components or port component configurations may be used, as desired.

In some embodiments, the balloon catheter 10 may be a cryotherapy balloon catheter and, in this embodiment, the balloon assembly 20 may be a cryo balloon configured to deliver cryotherapy to a treatment site internal to a patient. The cryo balloon assembly 20 may include at least one cooling region through which the cryotherapy can be delivered (or through which heat from adjacent body tissue can be extracted). In this example, the supply lumen 32 of the cryotherapy balloon catheter 10 may be configured to deliver fluid (e.g. cryogenic fluid) from external source 30 to the interior chamber 22 of the balloon assembly 20. As shown in FIG. 1, the supply lumen 32 may include a coiled portion 42 including one or more orifices (not shown) configured to release the cryogenic fluid in the interior chamber 22 of the balloon assembly 20. When so provided, at least some of the cryogenic fluid can undergo a liquid-to-gas phase change when released in the interior chamber 22 that cools the balloon assembly 20 by the Joule-Thomson effect. Gas resulting from the cryogenic fluid being released inside the chamber 22 can be exhausted through an exhaust lumen, such as lumen 36. The gas may be exhausted through the exhaust lumen 36 to the external vacuum pump 34.

As shown in FIG. 1, the coiled portion 42 of the supply lumen 32 may be helically wound around an inner tubular member (shown as 44 in FIG. 2) of the elongate shaft 12. In some cases, helically configuration of the coiled portion 42 of the supply lumen 32 may provide additional reinforcement to the inner tubular member. However, it is contemplated that the supply lumen 32 may be configured to include or not include a coiled portion, or have any other desired configuration. For example, supply lumen 32 may extend in a generally side-by-side or parallel arrangement with the inner tubular member, but this is just one example.

In some embodiments, the balloon catheter 10 may be an over-the-wire cryotherapy balloon catheter. In the illustrative example embodiment, the balloon catheter 10 may be advanced over a guidewire 11 to a desired location within a patient. To facilitate advancement of the balloon catheter 10 to the desired location, the catheter shaft 12 may define a guidewire lumen 38 for slidably receiving a guidewire 11. In some cases, the port component 31 may include a coupling for providing access to the guidewire lumen 38.

As shown in FIG. 1, the balloon catheter 10 can be disposed in a delivery sheath 26, however, it is contemplated that in other embodiments, the delivery sheath 26 may not be included. The illustrative delivery sheath 26 may be a hollow tube that can be initially placed inside a patient and subsequently used as a conduit for balloon catheter 10, as well as other medical devices. For example, when several catheters are used for a procedure, the delivery sheath 26 may help to protect the patient's internal body organs and/or body lumens through which the various medical devices are navigated. In addition, the delivery sheath 26 may also facilitate easier navigation of balloon catheter 10 and/or other medical devices by a physician or other technician to a treatment site.

In the illustrative embodiment, the delivery sheath 26 may be steerable, and it may be characterized by a specific diameter, length, distal feature, and/or other characteristics. For example, delivery sheaths may be available in varying diameters, such as, for example, 8.5 Fr (French), 10 Fr, 11 Fr.; varying lengths, such as, for example, 60 centimeters (cm), 65 cm, 71 cm, 78 cm, 90 cm.; and having distal ends that are biased in various shapes, such as, for example, in a 15 degree curve, a 55 degree curve, a short 120 degree curve, a long 120 degree curve. However, different delivery sheaths may be configured for different procedures, as desired. For example, a delivery sheath having one biased curvature may be particularly effective for guiding a cryo balloon to a patient's pulmonary veins to treat atrial fibrillation, while a delivery sheath having a different biased curvature may be particularly effective for another procedure, such as one in which a stent is delivered and positioned within a patient's vasculature.

As shown in FIG. 1, delivery sheath 26 may include a distal tip 27 that is slightly tapered to, for example, facilitate navigation of the distal sheath 26 through a patient's vasculature, or to facilitate crossing of tissue membranes of the patient (e.g. the septal wall during a procedure to treat atrial fibrillation). In some cases, the proximal end 28 of the delivery sheath 26 may be slightly flared or enlarged to more easily receive balloon catheter 10 and/or other medical devices.

Furthermore, the foregoing balloon catheter 10 and delivery sheath 26 are merely illustrative and are not meant to be limiting in any manner. It is contemplated that balloon catheter 10 may also include other components and/or structures that are typically found in balloon catheter or, more specifically, cryotherapy balloon catheters. For example, it is contemplated that balloon catheter 10 may include one or more sensors (e.g. temperature, pressure, etc) and sensor wires to monitor one or more parameters (e.g. temperature, pressure, etc) of the balloon catheter 10.

Figure 2:
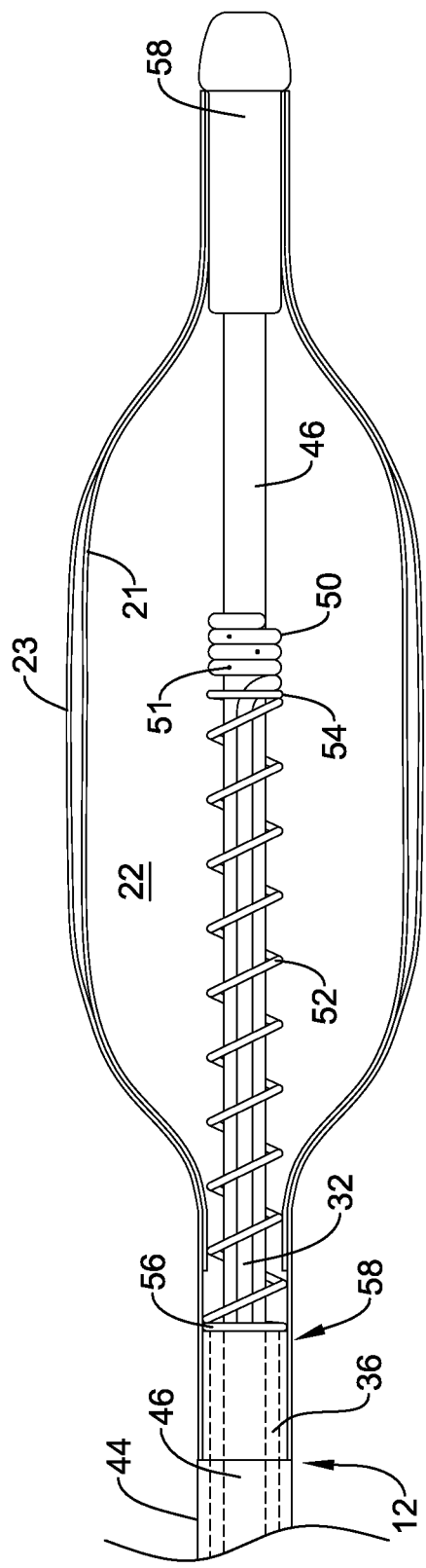
FIGS. 2 and 3 are a partial cut-away views of an illustrative biasing member that may be used in the balloon catheter shown in FIG. 1.
Figure 3:
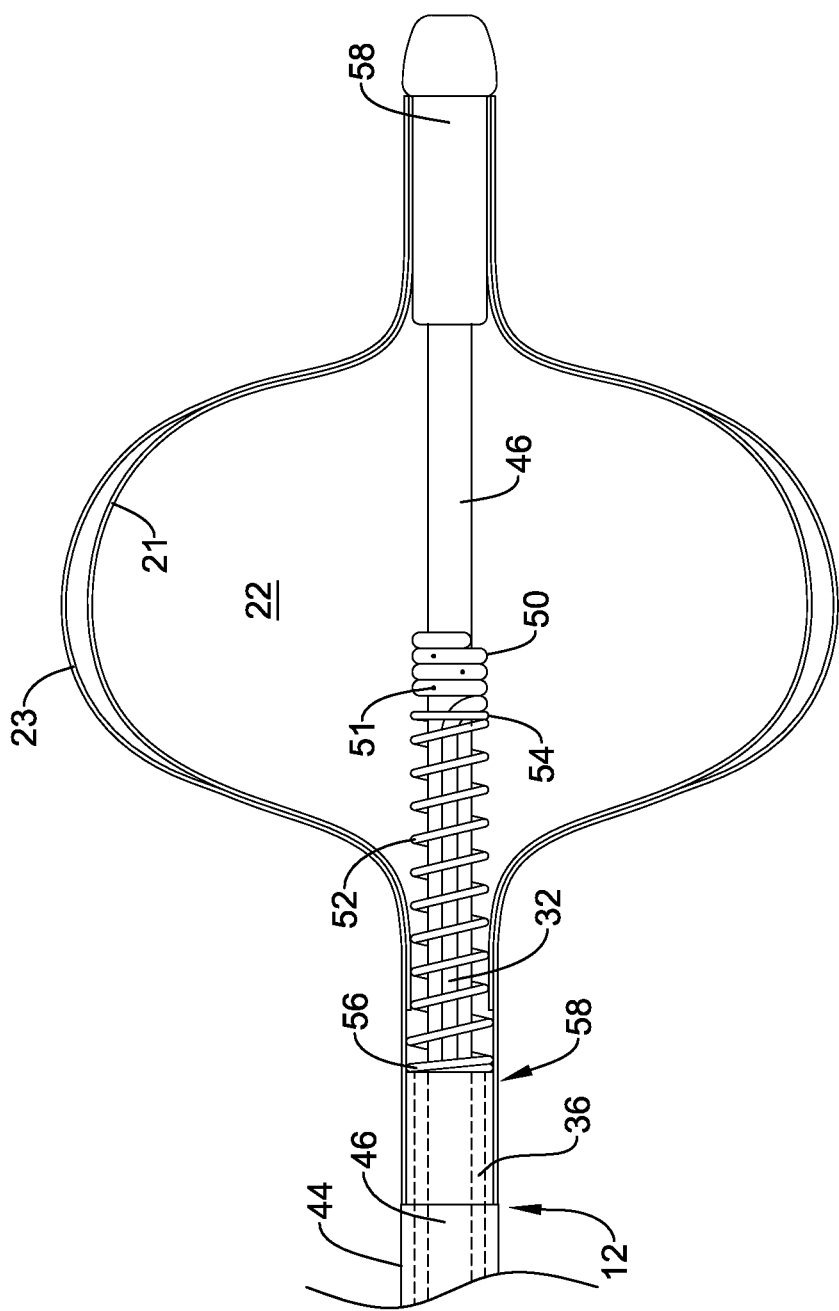
Figure 4:
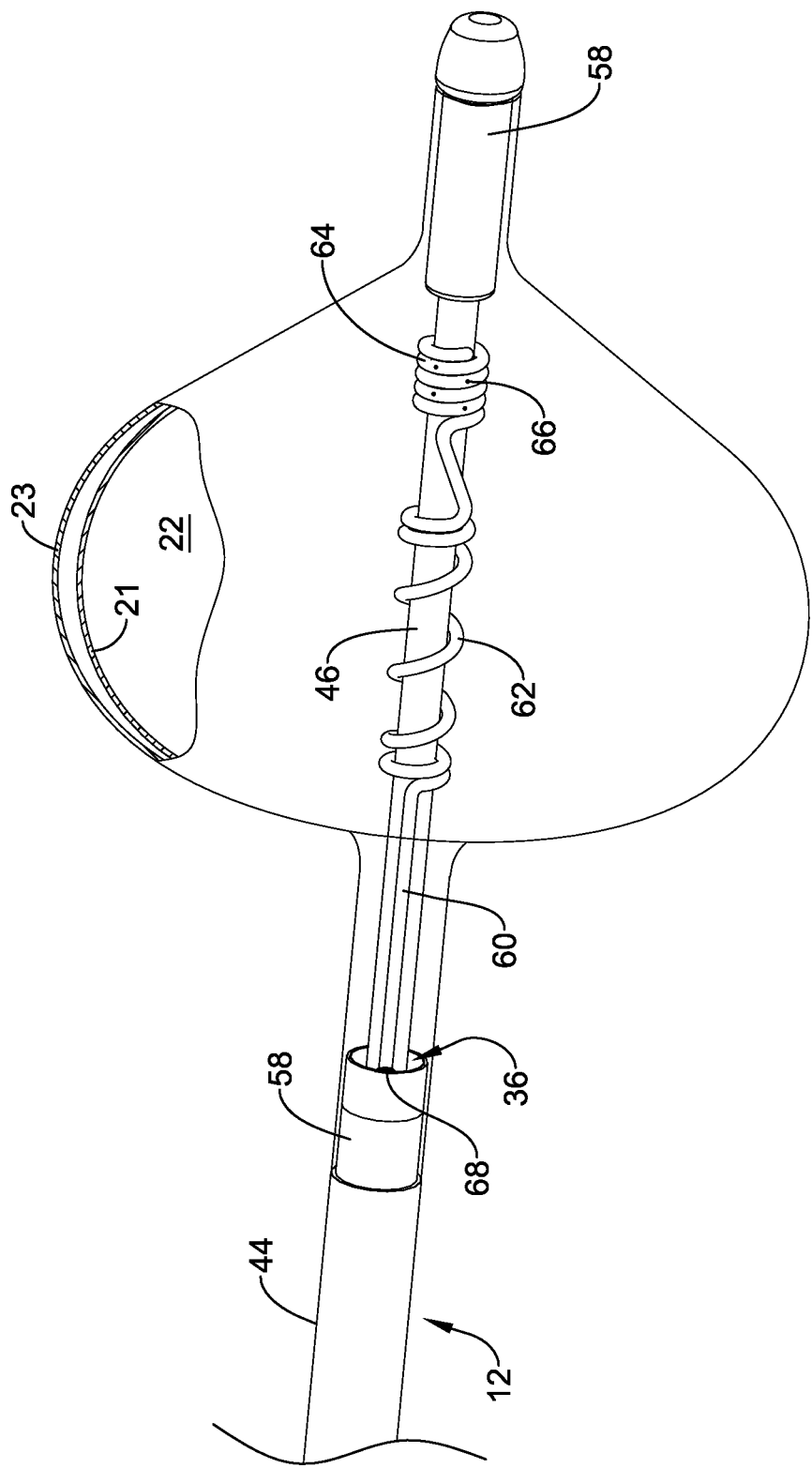
FIG. 4 is a partial cut-away view of another illustrative biasing member that may be used in the balloon catheter shown in FIG. 1.

Additionally, as shown in FIGS. 2-4, balloon catheter 10 may include a biasing member (shown as 52 in FIGS. 2 and 3) to bias the balloon assembly 20 to an extended configuration to facilitate delivery and/or withdrawal of the balloon catheter 10. For example, during a procedure, the balloon catheter 10 may be introduced to a treatment site inside a patient through guide catheter 26, and balloon assembly 20 can be inflated and used in delivering therapy. After the therapy is delivered at the treatment site, the balloon assembly 20 can be deflated, and the catheter 10 can be withdrawn from the patient through the guide catheter 26. However, in some instances, the balloon assembly 20 may bunch up or otherwise deflate to a diameter that is larger than its pre-inflation diameter. To help deflate the balloon assembly 20 and permit its withdrawal from the patient, the biasing member can bias the balloon assembly 20 to the extended state by exerting a distally-oriented force on the balloon assembly 20. Example biasing members are described with reference to FIGS. 2-4.

FIGS. 2 and 3 are partial cut-away views of an illustrative biasing member 52 that may be employed in the balloon catheter of FIG. 1. As shown in FIG. 2, the elongated shaft 12 may include an outer tubular member 44 and an inner tubular member 46 disposed within the outer tubular member 44. The inner tubular member 46 may define a guidewire lumen 38 and the annular-shaped space or lumen between the inner tubular member 46 and the outer tubular member 44 may define exhaust lumen 36. In some embodiments, the inner tubular member 46 and the outer tubular member 44 may be arranged such that the inner tubular member 46 extends distal of the outer tubular member 44. However, it is contemplated that other arrangements of the inner tubular member 46 and other tubular member 44 may be used, as desired.

In the illustrative embodiment, the outer tubular member 44 and inner tubular member 46 may be formed of suitable materials typically employed in catheter shafts. Example materials may include, for example, a polymer including but not limited to polyolefin copolymer, polyester, polyethylene teraphthalate, polyethylene, polyether-block-amide, polyamide (e.g. nylon), polyimide, latex, a urethane-family material, neoprene, etc. An example polyether-block-amide is available under the trade name PEBAX®. In some cases, the inner tubular member 46 may include a substantially non-compressible material (e.g., non-compressible, minimally compressible, or rigid, particularly in the longitudinal direction). Examples of substantially non-compressible materials can include, for example, braided materials (e.g., plastic tubes with embedded metal braiding) or hypotubes (e.g., steel hypotubes). However, the foregoing materials are merely illustrative and it is contemplated that any suitable materials may be used, as desired. In some embodiments, inner tubular member 46 and the outer tubular member 44 may be formed from the same or different material(s), as desired.

Furthermore, the foregoing elongate shaft 12 is merely illustrative and it is contemplated that other suitable elongate shafts may be used, as desired. In some cases, the elongate shaft may be a multi-lumen shaft defining one or more lumens of vacuum lumens, exhaust lumens, supply lumens, pressure lines, thermocouple lines, and/or other lumens or lines, as desired. An example multi-lumen shaft is disclosed in U.S. application Ser. No. 13/213,755, published as U.S. 2012/0150107, which is hereby incorporated by reference.

In the illustrative embodiment, a proximal end of the balloon assembly 20 may be bonded to the outer tubular member 44 and a distal end of the balloon assembly 20 may be bonded to the inner tubular member 46. In some cases, the outer balloon 23 may include a proximal waist bonded to an outer surface of outer tubular member 44 and the inner balloon 21 may include a proximal waist bonded to an inner surface of outer balloon 23. However, this is just one example bond and it is contemplated that other balloon bonding arrangement may be used. Some example bonding arrangements are disclosed in U.S. application Ser. No. 13/312,681, published as U.S. 2012/0143131, which is hereby incorporated by reference.

In some embodiments, a distal tip 58 may be disposed on the distal end of the inner tubular member 46. The distal tip 58 may include a lumen in fluid communication with guidewire lumen 38. In some cases, a distal waist of the inner balloon 21 may be bonded to the distal tip 58 and a distal waist of the outer balloon 23 may be bonded to the distal tip 58 and/or the distal waist of inner balloon 21. In other cases, the distal waist of the inner balloon 21 may be bonded directly to the inner tubular member 46 and the distal waist of the outer balloon 23 may be bonded to the inner tubular member 46 and/or distal waist of the inner balloon 21, as desired.

In the illustrative embodiment, supply lumen 32 may be disposed through the elongate shaft 12 and extend into the chamber 22 defined by balloon 21 to deliver a fluid (e.g., a cryogenic fluid) from external source 30 to the balloon assembly 20. The supply lumen 32 may be configured to release the fluid inside the interior chamber 22 of the balloon 20 via one or more orifices 51. Gas resulting from the cryogenic fluid being released inside the chamber 22 can be exhausted through exhaust lumen 36. As shown, the supply lumen 32 may include a distal region 50 coupled or connected to the inner tubular member 46. As shown in FIG. 2, the distal region 50 may be tightly wound around the inner tubular member 46 to secure it thereto. However, it is contemplated that other forms of connections, such as adhesive, may be used, as desired.

In the illustrative embodiment, biasing member 52 may be disposed in the chamber 22 of inner balloon 21. The biasing member 52 can include a proximal end 56 and a distal end 54. As shown in FIGS. 2 and 3, the proximal end 56 of biasing member 52 may be bonded, coupled, or otherwise connected to a distal end of outer tubular member 44. However, in other embodiments, it is contemplated that the proximal end 56 of the biasing member 52 may be connected to an outer surface of the outer tubular member 44. In some cases, the biasing member 52 may be configured so that it does not extend into and/or obstruct the exhaust lumen 36. The distal end 54 of the biasing member 52 may be bonded, coupled, or otherwise connected to the inner tubular member 46 at a location underneath the balloon assembly 20. As shown in FIGS. 2 and 3, the distal end 54 of the biasing 52 may be connected to the inner tubular member 46 proximal of the distal end 50 of the supply lumen 32, but this is not required.

In some embodiments, the biasing member 52 may be spring or coil. However, it is contemplated that any suitable structure that may exert a biasing force, such as compressive or expansive force, on the balloon assembly may be used. In some cases, the biasing member 52 may provide a distally-oriented longitudinal force to the inner tubular member 46 relative to the outer tubular member 44 to bias the balloon assembly 20 into a longitudinally extended configuration. In other words, the biasing member 52 may be configured to apply a distally-oriented longitudinal force to the balloon assembly 20 through the catheter shaft 12 so that the majority of the compression force of the biasing member 52 is applied to the balloon assembly 20.

In the illustrative embodiment, the biasing member 52 may be configured to include any suitable material have a spring constant. Example materials may include, but are not limited to nickel-titanium alloys (such as Nitinol) and stainless steels. However, it is contemplated that other suitable materials may be used, as desired.

As shown in FIG. 2, when the balloon assembly 20 is not inflated, the balloon assembly 20 may be in a longitudinally extended (and radially unexpanded) state. As shown in FIG. 3, when the balloon assembly 20 is inflated with the cooling fluid, the spring member 52 is compressed, and the balloon assembly 20 is in a radially expanded (longitudinally compressed) state. In this state, the cooling fluid may exert a force overcoming the biasing force of the biasing member 52. When the cooling fluid is exhausted, such as via exhaust lumen 36, the balloon assembly 20 may return to the longitudinally extended (and radially unexpanded) state, as shown in FIG. 2.

FIG. 4 is a partial cut-away view of another illustrative biasing member 62 that may be used in the balloon catheter shown in FIG. 1. In the illustrative embodiment, the biasing member 62 may be formed or otherwise incorporated into the supply lumen 60 of the catheter shaft 12. As shown in FIG. 4, the supply lumen 60 may include a distal end 64 that is tightly would and attached to the inner tubular member 46, similar to distal end 54 of supply lumen 32. The distal end portion 64 may also include orifices 66 to deliver the fluid to chamber 22. However, in this embodiment, the biasing member 62 may be formed from a portion of the supply lumen 60 that is positioned beneath the balloon assembly 20. As shown, the biasing member 62 may be coiled around the inner tubular member 46 and may provide a compressive or expansive force on the balloon assembly 20, similar to biasing member 52.

In the illustrative embodiment, the supply lumen 60 may be connected to the outer tubular member 44 by bond 68, which may be proximal of the biasing member 62 portion. As shown, bond 68 is at a distal end of outer tubular member 44, however, it is contemplated that bond 68 may be positioned at other locations along the length of outer tubular member 44, as desired. In some cases, bond 68 may include an adhesive. However, other types of bonds may be used, as desired. In the illustrative embodiment, supply lumen 60 may be connected to inner tubular member 46 distal of the biasing member 62 portion. For example, supply lumen 60 may be connected to inner tubular member 46 in the distal end 64.

In the illustrative embodiment, when the balloon assembly 20 is not inflated, the balloon assembly 20 may be in a longitudinally extended (and radially unexpanded) state, such as shown in FIG. 4. When the balloon assembly 20 is inflated with the cooling fluid, the biasing member 62 can be compressed, and the balloon assembly 20 can be moved to a radially expanded (longitudinally compressed) state. In this state, the cooling fluid may exert a force overcoming the biasing force of the biasing member 62. When the cooling fluid is exhausted, such as via exhaust lumen 36, the balloon assembly 20 may return to the longitudinally extended (and radially unexpanded) state, again as shown in FIG. 4.

Having thus described the preferred embodiments of the present disclosure, those of skill in the art will readily appreciate that yet other embodiments may be made and used within the scope of the claims hereto attached. Numerous advantages of the disclosure covered by this document have been set forth in the foregoing description. It will be understood, however, that this disclosure is, in many respect, only illustrative. Changes may be made in details, particularly in matters of shape, size, and arrangement of parts without exceeding the scope of the disclosure. The invention's scope is, of course, defined in the language in which the appended claims are expressed.

What is claimed is:

1. A medical device comprising:
   an inner tubular member including a proximal region and a distal region;
   an outer tubular member disposed about the inner tubular member, the outer tubular member including a proximal region and a distal region;
   a balloon assembly, the balloon assembly including a proximal waist coupled to the distal region of the outer tubular member and a distal waist coupled to the distal region of the inner tubular member, the balloon assembly defining a chamber configured to receive a fluid; and
   a fluid supply tube positioned between the inner tubular member and the outer tubular member, the fluid supply tube including a proximal end configured to couple to a cooling source and a distal end configured to deliver the fluid to the chamber of the balloon assembly, wherein the fluid supply tube is directly connected to the distal region of the outer tubular member and to the distal region of the inner tubular member, wherein the fluid supply tube includes a coiled portion positioned in the chamber of the balloon assembly.

2. The medical device of claim 1, wherein the coiled portion of the fluid supply tube is configured to bias the balloon assembly to a longitudinally extended state.

3. The medical device of claim 2, wherein the coiled portion of the fluid supply tube is configured to be compressed when the balloon is inflated with the fluid.

4. The medical device of claim 1, wherein the coiled portion of the fluid supply tube is wound around inner tubular member.

5. The medical device of claim 1, wherein the balloon assembly includes an outer balloon disposed around an inner balloon.

6. The medical device of claim 1, wherein the medical device is configured to perform cryotherapy.

7. A method of biasing a balloon catheter, the method comprising:
   providing a catheter shaft including an outer tubular member disposed around an inner tubular member;
   coupling a proximal waist of a balloon assembly to the outer tubular member and a distal waist of the balloon assembly to the inner tubular member, wherein the balloon assembly defined a chamber;
   biasing the balloon assembly to a longitudinally extended state with a biasing member positioned in the chamber of the balloon assembly, wherein the biasing member is directly connected to the outer tubular member and the inner tubular member and positioned in the chamber of the balloon assembly, wherein a distal end of the biasing member is proximal of the distal end of the balloon assembly; and
   moving the balloon assembly from the longitudinally extended state to a radially expanded state by delivering fluid to chamber of the balloon assembly to overcome the bias of the biasing member.

8. The method of claim 7, further comprising moving the balloon assembly from the radially expanded state to the longitudinally extended state by exhausting the fluid from the chamber balloon assembly.

9. The method of claim 7, wherein the biasing member is a spring.

10. The method of claim 7, wherein the biasing member includes a coiled portion of a fluid supply tube, wherein the fluid supply tube has a proximal end configured to couple to a cooling source and a distal end configured to deliver a cooling fluid to the chamber defined by the balloon assembly.

11. The method of claim 7, wherein the balloon assembly is a dual balloon assembly.

* * * * *